United States Patent [19]

Tomiya et al.

[11] Patent Number: 5,162,866
[45] Date of Patent: Nov. 10, 1992

[54] APPARATUS AND METHOD FOR INSPECTING IC LEADS

[75] Inventors: Hiroshi Tomiya, Tokyo; Hideharu Ohashi; Masato Takayama, both of Kanagawa, all of Japan

[73] Assignee: Sony Corporation, Tokyo, Japan

[21] Appl. No.: 631,244

[22] Filed: Dec. 20, 1990

[30] Foreign Application Priority Data

Dec. 25, 1989 [JP] Japan .................. 1-335970

[51] Int. Cl.$^5$ .............. G01N 21/00; G01N 21/86
[52] U.S. Cl. .................. 356/237; 356/398; 250/561
[58] Field of Search ............. 356/237, 376, 394, 398, 356/380, 384, 386, 387, 375; 250/562, 563, 572, 561; 382/61, 8; 358/101, 106, 107

[56] References Cited

U.S. PATENT DOCUMENTS

| | | | |
|---|---|---|---|
| 4,379,175 | 4/1988 | Tamura | 250/561 |
| 4,598,998 | 7/1986 | Kamei et al. | 356/376 |
| 4,765,744 | 8/1988 | Kobayashi | 356/398 |

FOREIGN PATENT DOCUMENTS

| | | | |
|---|---|---|---|
| 0233304 | 10/1986 | Japan | 356/237 |
| 63-278345 | 11/1988 | Japan | |
| 1-272126 | 10/1989 | Japan | |

Primary Examiner—Richard A. Rosenberger
Assistant Examiner—Hoa Pham
Attorney, Agent, or Firm—Hill, Van Santen, Steadman & Simpson

[57] ABSTRACT

An IC lead inspecting apparatus and a method of using such apparatus to measure any pitch deviation or coplanarity error of each IC lead. The apparatus comprises at least a displacement sensor for irradiating inspection light onto both an IC setting table and leads of an IC placed on the table so as to be inspected, and detecting the reflected light therefrom to measure the heights of the leads; and scanning means for moving the displacement sensor and the IC setting table relative to each other and scanning the lead array of the IC by the inspection light, wherein reference marks are formed on a scanning line of the inspection light on the IC setting table, and a surface portion of the table is composed of a transparent material. The pitch deviation of each lead is measured on the basis of a timing change in the output signal of the displacement sensor. And the upward or downward coplanarity error of each lead is measured from a level change in the output signal of the sensor.

16 Claims, 1 Drawing Sheet

APPARATUS AND METHOD FOR INSPECTING IC LEADS

BACKGROUND OF THE INVENTION

The present invention generally relates to apparatus for inspecting integrated circuit (IC) leads. More particularly, the invention relates to an IC lead inspecting apparatus that comprises: at least a displacement sensor for irradiating inspection light onto both an IC setting table and leads of an IC placed thereon to be inspected, and then detecting reflected light to measure the heights of the leads; and a scanning means for moving the displacement sensor relative to the IC setting table and scanning the IC leads by the inspection light. The present invention relates also to a method for inspecting IC leads through measuring the pitch deviation and the coplanarity error of each lead by the use of such inspecting apparatus.

There is a trend toward increased production and supply of QFP ICs to meet the recent rising demand therefor. Consequently, it has become necessary to expedite inspection of a larger quantity of QFP ICs after completion of manufacture. In addition to inspecting the electric characteristics of the ICs, it is considered important to inspect the presence or absence of any deformation in the leads of each QFP IC.

One deformation is pitch error and this refers to skewing of one or more leads or lateral aberrations thereon. Another deformation is coplanarity deformation and this refers to upward or downward bending of one or more leads, when an IC is viewed in plan view. Coplanarity can also refer to leads surface aberrations such as undue roughness.

Due to a numerical increase of leads resulting from the recent progress with regard to high integration density of QFP ICs, the dimensions of the leads and the pitches thereof (i.e., distances between leads) have become smaller, so that even a slight pitch deviation or coplanarity error of a lead deteriorates the mateability between a QFP IC and a wiring film on a printed circuit board to which the QFP IC is connected. It is therefore necessary to be able to inspect the ICs with extreme precision, and this requisite is not met by visual inspection. Further, a satisfactory inspection result is not achievable by sampling inspection alone. Entire productions need to be inspected, this meaning that a great quantity of ICs must be inspected.

In view of such circumstances, apparatus have been developed for lead deformation inspection which employ an image processing system or an optical displacement sensor. Such apparatus are disclosed in Japanese Patent Laid-open No. Hei 1 (1989)-272126 (JP 1272126), the teachings of which are incorporated herein by reference, and No. Sho 63 (1988)-278345 (JP 63278345), the teachings of which are also incorporated herein by reference.

The image processing system of JP 63278345 requires a prolonged signal processing time and therefore has difficulty in meeting the requirement of inspecting a large quantity of QFP ICs. Furthermore, although the inter-lead pitch deviation can be measured by means of an image pickup camera operated above a QFP IC, the upward or downward coplanarity error of each lead cannot be inspected unless an end face image of the lead is picked up by a camera operated beside the QFP IC. Yet further, in inspecting the coplanarity errors on the four sides of the leads, these steps must be repeated four times. Consequently, the time required for inspecting each QFP IC is rendered extremely long.

In the lead deformation inspecting apparatus with an optical displacement sensor disclosed in JP 1272126, a complicated process of image recognition is not necessary, and inspection can be executed in a real time mode merely by processing an electric signal output from an optical displacement sensor, so that both the coplanarity error and the pitch deviation of each lead can be inspected simultaneously by a single displacement sensor, this consequently expediting the operation. In this respect, this system is considered to be advantageous.

In the lead deformation inspecting apparatus of JP 1272126, the sensor includes a light source for emitting a beam of laser light or the like, and a light receiving element, such as a photosensitive diode (PSD), for sensing the light emitted originally from the source and reflected by the lead (or base surface), wherein an output signal of the light receiving element is processed to measure the pitch deviation (deformation in the planar direction of the lead) and the coplanarity error (deformation in the vertical direction of the lead). The principle of such lead deformation inspection is briefly described below.

First, the pitch deviation (deformation in the planar direction of the lead, defect in a lateral portion thereof, or adhesion of extraneous substance thereto) is inspected by relying on the fact that the light emitted from the light source is reflected at different heights depending on the lead and the IC setting table. Such reflection height difference is detected by the displacement sensor, and the inspection is achieved by measuring the timing of the level change caused in the output signal of the displacement sensor by scanning with the inspection light.

The upward or downward coplanarity error (deformation in the vertical direction of the lead) is inspected by first detecting the difference between the heights of the lead and the surface of the IC setting table by means of the displacement sensor and then recognizing the height of the lead on the basis of such difference.

However, in this IC lead inspecting system, the dynamic range of the output signal of the displacement sensor is narrow. This phenomenon is derived from the fact that, since the lead is as thin as 0.1 mm or less, merely a small difference occurs between the output signal of the displacement sensor obtained at the time of scanning the lead surface and the output signal at the time of scanning any positioned space apart from the lead (i.e., the surface of the IC setting table).

With respect to the pitch deviation of the leads, the inter-lead positional correlationship is determined at the beginning and, if any unallowable abnormality exists in such positional correlationship, the condition is regarded as an abnormal state for the first time. Accordingly, when all of the leads on one side of an IC are deformed in parallel with one another, such condition is not regarded as an abnormal state. Such failure to be able to recognize this defect is disadvantageous.

The problem concerning the narrow dynamic range of the output signal of the displacement sensor ca be solved if the surface portion of the IC setting table is composed of a transparent material. Such a solution is composed of a transparent material. Such a solution is disclosed also in Japanese Patent Laid-open No. Hei 1 (1989)-272126. However, in the disclosed structure where the surface portion of the IC setting table is made of a transparent material, a base point for use as a reference for determining the coplanarity error does not exist. Therefore, coplanarity error must be inspected by comparing the heights of the individual leads with one another in a manner similar to inspection of the lead pitch deviation. Consequently, if all of the leads on one side of an IC have the same coplanarity error, it is impossible to recognize such IC as a defective.

SUMMARY OF THE INVENTION

The present invention provides an apparatus and a method capable of precisely inspecting IC leads to discriminate between satisfactory and defective ones by detecting the absolute values of pitch deviations and coplanarity errors of the IC leads. To this end, reference marks are formed on an inspection light scanning line on an IC setting table and a surface portion of the table is composed of a transparent material.

According to one aspect of the present invention, there is provided an IC lead inspecting apparatus comprising a displacement sensor for irradiating inspection light onto both an IC setting table and leads of an IC placed on the table, and detecting light reflected therefrom to measure the heights of the leads; and a scanning means for moving the displacement sensor and the IC setting table relatively to each other so that the lead array of the IC can be scanned by the inspection light. Since reference marks are formed on an inspection-light scanning line on the IC setting table, it becomes possible to detect the absolute planar position of each lead by utilizing the reference marks as base points. Consequently, even when all leads on one side of an IC are deformed in parallel with one another, the IC can still be recognized as a defective.

According to another aspect of the present invention, there is provided a method of inspecting IC leads by the use of the above apparatus to measure the pitch deviation of each lead on the basis of a timing change in the output signal of the displacement sensor. Since a surface portion of the IC setting table is composed of a transparent material, the height of reflection of an inspection laser beam through the inter-lead space can be lowered below the surface of the IC setting table, thereby widening the dynamic range of an output signal of the displacement sensor. Furthermore, due to the provision of reference marks on an inspection-light scanning line on the IC setting table, the absolute upward or downward coplanarity error of each lead can be measured by using the reference marks as base points. Therefore, it is possible to detect a defective IC even where all of the leads on one side thereof have the same coplanarity error.

The above and other features of the present invention will become apparent from the following detailed description of the presently preferred embodiments and the accompanying drawings.

DETAILED DESCRIPTION OF THE PRESENTLY PREFERRED EMBODIMENTS

Figure 1:
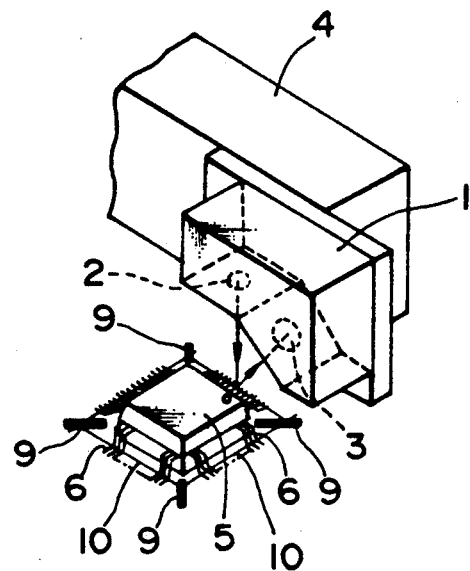
FIG. 1 is a perspective view of an IC lead inspecting apparatus embodying the present invention.
Figure 2:
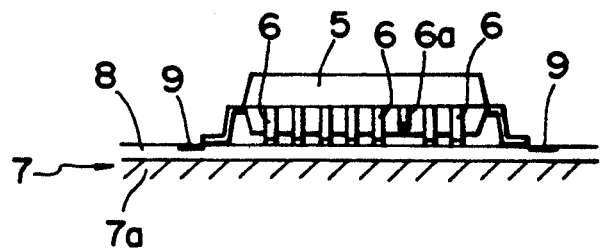
FIG. 2 is a sectional view of an IC setting table employed in the embodiment of FIG. 1.

As illustrated in FIG. 1, an IC lead inspecting apparatus includes, an optical displacement sensor 1, where a laser beam source 2 is disposed in a lower horizontal portion, and an optical position sensing element (PSD) 3 is disposed in an oblique portion so as to be at an adequate angle to the lower horizontal portion. The optical position sensing diode (PSD) 3 is used as a light receiving element and serves to detect height when an inspection light beam emitted from the laser beam source 2 is reflected by a lead or the IC setting table. Due to such detection of height, it becomes possible to detect the positional errors of the leads in both the planar and vertical directions thereof.

The optical displacement sensor 1 is attached to an arm 4 and is moved by a driving mechanism (not illustrated) in such a manner as to scan lead arrays 6 on an IC such as QFP IC 5 by an inspection laser beam emitted from the laser beam source 2.

The QFP IC 5 is placed on the IC setting table 7 so as to be inspected. The table 7 comprises an IC setting table body 7a composed of a white ceramic material or the like, and a glass plate 8 having a predetermined thickness for example, of 3 mm, and attached to the surface of the table body 7a. Such a structure is formed for the purpose of widening the dynamic range of an output signal of the displacement sensor 2. This technique is disclosed in the aforementioned Japanese Laid-open Patent No. Hei 1 (1989)-272126.

With an IC lead inspecting apparatus equipped with such displacement sensor, any pitch deviation of each lead in the planar direction can be detected by utilizing the difference between the height of the inspection laser beam reflected from the lead and that reflected from the IC setting table. However, the leads 6 that have been produced under the latest technological advances generally have a small thickness, e.g., 0.1 mm or so, in most cases, are likely to be thinner in the future. Therefore, the spatial difference between the surface of the lead 6 and the surface of the IC setting table 7 must be extremely small, e.g., 0.1 mm or so. Consequently, the difference between the output signal of the displacement sensor 1 obtained by scanning the lead 6 by the inspection laser beam and that obtained by scanning the IC setting table 7, is a very small value corresponding to the thickness of the lead. In other words, the dynamic range of the sensor output signal is extremely narrow.

With the dynamic range of the output signal of the displacement sensor 1 being so narrow, it becomes difficult to set a threshold voltage when converting the output signal into a binary value. Further detection errors due to noise interference are prone to occur.

Under such circumstances, if a surface portion of the IC setting table 7 comprises a transparent plate 8, the difference between the height of reflection of an inspection laser beam scanning the surface of the lead 6 and that scanning the IC setting table 7 is rendered greater by an amount corresponding to the thickness of the transparent plate 8. This increases or widens the dynamic range of the output signal. Consequently, the threshold voltage for converting the output signal into a binary value can be more easily set to eventually prevent unwarranted detection of error. Further, the output is rendered less susceptible to noise interference. For the foregoing reasons, the transparent plate 8 is used to form a surface portion of the IC setting table 7.

The IC setting table 7 not only uses the transparent plate 8 as its surface portion but also includes reference marks 9 composed of, for example, aluminum and having a thickness of several hundred angstroms, provided on the surface of the transparent plate 8. The reference marks 9 are disposed on a scanning line of an inspection laser beam, so that such reference marks 9 are also scanned by the laser beam together with the leads 6 being inspected. The QFP IC 5 to be inspected needs to be placed on the IC setting table 7 in a manner to retain a predetermined positional relationship with respect to the reference marks 9 because a decision as to whether any improper pitch deviation is existent or not in each lead 6 of the QFP IC 5 is made by first measuring the space between the reference marks 9 and the leads 6 and then determining if the measured value is abnormal or not.

The marks 9 are utilized not only as references in determining defective leads 6 relative to pitch deviations thereof, but also as references in detecting the heights of the leads 6 relative to upward or downward coplanarity errors thereof. To this end, the reference marks 9 are formed on the surface of the transparent plate 8 to serve as height references, and the absolute heights of the individual leads 6 can be determined depending on the heights of the leads 6 from such references.

The reference marks 9 are formed by evaporating aluminum or the like. For the purpose of ensuring complete adhesion to the base, grooves are formed in the base portions where the reference marks 9 are to be provided, thereby roughening the base surface. The reference marks 9 are then formed in the roughened portions.

It can be appreciated that such a roughening step is not an absolute requisite. Further, the material of the marks is not limited to aluminum and may be any other suitable material that has a sufficient reflectivity. For example, the reference marks 9 may be composed of chromium or the like, and each mark may be in any suitable shape such as a tape, a cross, or any other adequate shape.

Figure 3:
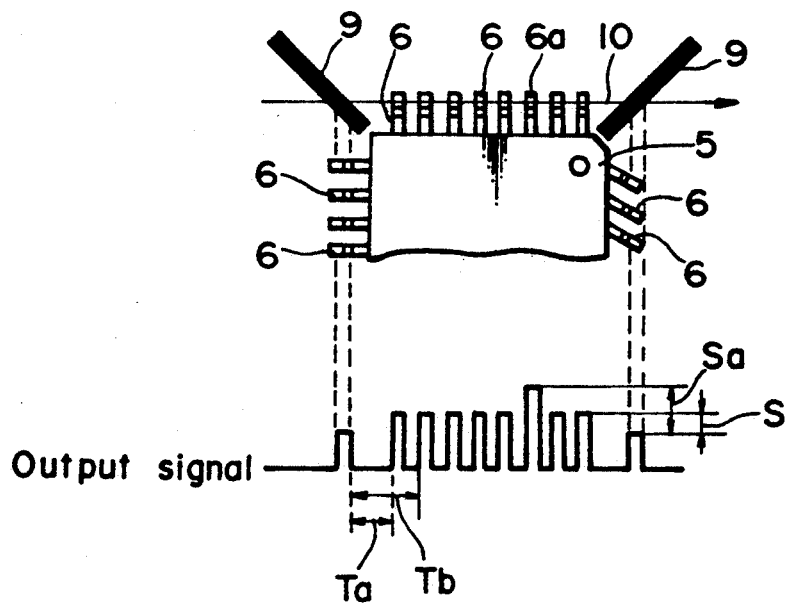
FIG. 3 illustrates the relationship between leads and an output signal of a displacement sensor in the embodiment of FIG. 1.

Referring now to FIG. 3, changes caused in the output signal will be described below specifically.

When an inspection laser beam is emitted to scan along a line 10, a pulse (whose waveform may not exactly be as that shown) is generated in the output signal every time the laser beam passes through the reference mark 9 and the lead 6. The distance between each lead 6 and the reference mark 9 can be determined from the time difference Ta (Tb, ...) between the pulse generated upon passage of the inspection laser beam through each lead 6 and the pulse generated upon passage of the beam through the reference mark 9. In the apparatus disclosed in JP 1272126, a decision is made merely with regard to the relative distance between the leads 6 and therefore in the exemplary case of FIG. 3 where all of the leads 6 on the right side of the IC 5 are deviated (skewed) in parallel with one another, such a state cannot be recognized as a defective one. However, due to the provision of reference marks 9 serving as base points, the absolute planar positions of the leads 6 can be measured according to the present invention, so that even in such exemplary case, the QFP IC 5 is properly recognized as a defective.

In deciding the upward or downward coplanarity errors of the leads 6 the absolute height of each lead 6 can be determined from the difference S between the level of the pulse generated upon passage of the inspection laser beam through the reference marks 9 and the level of the pulse generated upon passage of the beam through each lead 6. Therefore, if one lead 6a has an upward coplanarity error, the pulse level corresponding to such lead 6a becomes higher than any of the pulse levels corresponding to the other leads 6 whereby the difference Sa between such higher pulse level and the pulse levels corresponding to the reference marks 9 becomes greater to consequently indicate an abnormal state.

When all of the leads 6 on one side of the QFP IC 5 have upward or downward coplanarity errors, the presence or absence of any improper height can be determined by detecting the height of each lead 6 from the height difference between the reference marks 9 and each lead 6, whereby the leads on the inspected side can be regarded as defective ones.

The technique of determining the heights of the leads 6 in accordance with the reference marks 9 brings about the advantage that any variation in the height of the displacement sensor 1 to the IC setting table 7 is not a factor that deteriorates the inspection accuracy. More specifically, since the output signal of the displacement sensor 1 varies in conformity with the height thereof relative to the IC setting table 7, there naturally occur errors due to the height variations of the displacement sensor 1 in cases none of height references such as the marks 9 is provided. Consequently, in a system employing different inspection states with regard to the leads 6 on the individual sides of the QFP IC 5, some errors may be induced depending on the sides of one QFP IC 5 if any height variation is existent between the inspection stages. However, if merely the height of the reference marks 9 to the surface of the transparent plate 8 is kept constant (in this embodiment, if the reference mark 9 is at the same height as the surface of the transparent plate 8), the height variation, if any, of the displacement sensor 1 to the IC setting table 7 is not a factor that causes an error.

In the embodiment discussed above, the reference marks 9 are formed on the surface of the transparent plate 8. However, the position of each reference mark 9 is not limited to the above example alone, and the mark may be formed at an intermediate depth of the transparent plate 8 as well as on the surface thereof.

As described above, when reference marks are provided on an inspection-light scanning line on an IC setting table, the planar positional relationship between each lead and the reference marks can be detected. It becomes possible to detect the absolute planar position of each lead while utilizing the reference marks as base points. Consequently, when all of the leads on one side are deformed in parallel with one another, the IC can still be recognized as a defective.

When a surface portion 8 of the IC setting table comprises a transparent material, the height of reflection of an inspection laser beam through the inter-lead space can be lowered below the surface of the IC setting table, thereby widening the dynamic range of an output signal of the displacement sensor. Furthermore, due to the provision of reference marks on an inspection-light scanning line on the IC setting table, the absolute upward or downward coplanarity error of each lead can be measured by using the reference marks as base points. Therefore, it is possible to achieve exact detection of any defective IC where the entire leads on one side thereof have the same upward or downward coplanarity error.

While preferred embodiments have been described, modifications and changes may become apparent to those skilled in the art which shall fall within the spirit and scope of the invention. It is intended that such modifications and changes be covered by the attached claims.

We claim

1. An IC lead inspection device comprising:
   a table on which is positioned an IC whose leads are to be inspected;
   a displacement sensor supported above a top surface of the table, said sensor operative to irradiate a scan beam onto said table and to receive and detect light reflected therefrom to measure relative heights of said leads, said displacement sensor being displaced along a path such that said scan beam is directed along a scan line coincident with said leads; and
   reference marks provided on said top surface of the table along said scan line, said reference marks providing base points against which height and pitch deviations of said IC leads can be measured.

2. The IC lead inspection device of claim 1 wherein said reference marks are disposed within the table below the top surface thereof.

3. An IC lead inspection device comprising:
   a table on which is positioned an IC whose leads are to be inspected;
   a displacement sensor supported above a top surface of the table, said sensor operative to irradiate a scan beam onto said table and to receive and detect light reflected therefrom to measure relative heights of said leads, said displacement sensor being displaced along a path such that said scan beam is directed along a scan line coincident with said leads, said top surface comprising transparent material; and
   reference marks provided on said top surface along said scan line, said reference marks providing base points against which heights and pitch deviations of said IC leads can be measured.

4. An IC lead inspection device comprising:
   a table on which is positioned an IC whose leads are to be inspected;
   a displacement sensor supported above a top surface of the table, said sensor operative to irradiate a scan beam onto said table and to receive and detect light reflected therefrom to measure relative heights of said leads, said scan being directed along a scan line coincident with said leads; and
   reference marks provided on said top surface along said scan line said reference marks being made of aluminum.

5. An IC lead inspection device comprising:
   a table on which is positioned an IC whose leads are to be inspected;
   a displacement sensor supported above a top surface of the table, said sensor operative to irradiate a scan beam onto said table and to receive and detect light reflected therefrom to measure relative heights of said leads, said scan beam being directed along a scan line coincident with said leads, said top surface comprising transparent material; and
   reference marks provided on said top surface along said scan line, said reference marks comprising aluminum deposited thereon.

6. A method for inspecting IC leads, comprising the steps of:
   providing an IC testing table having reference marks therein and arranged on a line, said reference marks providing base points against which deviations in height and pitch of leads of said IC can be measured;
   providing a displacement sensor operative to irradiate a top surface of the table with a scan beam and to receive reflected light so as to measure vertical displacement along said top surface;
   positioning an IC on said table such that an array of leads of said IC are positioned between two reference marks;
   displacing said displacement sensor along a path such that said scan beam is displaced along a scan line along said top surface, said scan line being coincident with said array of leads of said IC;
   detecting at least one of said reference marks with said displacement sensor;
   detecting said leads with said displacement sensor; and
   calculating deviations between each lead in said array and said one reference mark.

7. The method of claim 6, wherein said lead deviations comprise pitch errors.

8. The method of claim 6, wherein said deviations comprise coplanarity errors.

9. The method of claim 6, wherein the step of calculating deviations comprises calculating height differences between said reference mark and said leads.

10. A method for inspecting IC leads, comprising the steps of:
    providing an IC testing table having reference marks therein and arranged along a line, said reference marks providing points against which deviations in height and pitch of leads of said IC can be measured;
    providing a displacement sensor operative to irradiate a top surface of the table with a scan beam and to receive reflected light so as to measure vertical displacement along said top surface;
    positioning an IC on said table such that an array of leads of said IC are positioned between two reference marks;
    displacing said displacement sensor along a path such that said scan beam is displaced along a scan line along said top surface, said scan line being coincident with said array of leads of said IC;
    detecting at least one of said reference marks with said displacement sensor;
    identifying a time for said detection of said one reference mark;
    detecting said leads with said sensor;
    identifying a time for detection of each leads; and
    calculating deviations between each lead and said one reference mark.

11. The method of claim 10, wherein the step of calculating deviations comprises calculating time differences between detection of said reference mark and detection of said leads.

12. An IC lead inspection device comprising:
    an IC testing table having a surface on which an IC is positioned for inspection, said surface having a transparent section, said transparent section including at least one reference mark therein;
    a displacement sensor positioned above the table and operative to generate a scan beam and to receive light reflected from said table surface; and means for displacing said displacement sensor along a path such that said scan beam follows a path across said reference mark and an array of leads of an IC positioned on said table, said reference mark providing a base point against which height and pitch deviations of said leads can be measured.

13. The device of claim 12, wherein four such reference marks are provided.

14. The device of claim 12, wherein said reference marker is made of a reflective material.

15. The device of claim 12, wherein the reflective material is aluminum.

16. The device of claim 15, wherein the reflective material is chromium.

* * * * *